US007893031B2

(12) United States Patent
Yoshida et al.

(10) Patent No.: US 7,893,031 B2
(45) Date of Patent: Feb. 22, 2011

(54) NEURONAL DIFFERENTIATION INHIBITOR PEPTIDE AND USE THEREOF

(75) Inventors: Tetsuhiko Yoshida, Nagoya (JP); Nahoko Kobayashi, Nagoya (JP); Hiroshi Kanno, Yokohama (JP)

(73) Assignee: Toagosei Co., Ltd., Minato-ku (JP)

( * ) Notice: Subject to any disclaimer, the term of this patent is extended or adjusted under 35 U.S.C. 154(b) by 172 days.

(21) Appl. No.: 12/088,974

(22) PCT Filed: Oct. 3, 2006

(86) PCT No.: PCT/JP2006/319748
§ 371 (c)(1),
(2), (4) Date: Apr. 2, 2008

(87) PCT Pub. No.: WO2007/040212
PCT Pub. Date: Apr. 12, 2007

(65) Prior Publication Data
US 2009/0270334 A1 Oct. 29, 2009

(30) Foreign Application Priority Data
Oct. 5, 2005 (JP) .............................. 2005-293071

(51) Int. Cl.
A01N 37/18 (2006.01)
A61K 38/00 (2006.01)
C07K 16/00 (2006.01)
(52) U.S. Cl. ..................... 514/21.5; 514/21.3; 530/300; 530/324; 530/326
(58) Field of Classification Search ........................ None
See application file for complete search history.

(56) References Cited

U.S. PATENT DOCUMENTS 6,084,068 A * 7/2000 Conaway et al. ............ 530/350
2007/0065941 A1 3/2007 Kondo et al.

FOREIGN PATENT DOCUMENTS

| EP | 1849474 | 10/2007 |
|---|---|---|
| JP | 09-323928 | 12/1997 |
| JP | 2001501477 | 2/2001 |
| JP | 2003514765 | 4/2003 |
| JP | 2005-330206 | 12/2005 |
| WO | 9814574 | 4/1998 |
| WO | 00/62067 | 10/2000 |
| WO | 0062067 | 10/2000 |
| WO | 2006/088010 | 8/2006 |

OTHER PUBLICATIONS

International Search Report for PCT/JP2006/319748 dated Dec. 26, 2006.
European Search Report dated Mar. 19, 2009 corresponding to U.S. Appl. No. 12/088,974, filed on Apr. 2, 2008.
Takumi kamura, et al, "MUF1, A Novel Elongin BC-interacting Leucine-rich Repeat Protein That Can Asseble with Cul5 and Rbx1 to Reconstitute a Ubiquitin Ligase," Journal of Biological Chemistry, vol. 276, No. 32, pp. 29748-79753, Aug. 10, 2001.
Adam Kibel, et al, "Binding of the von Hippel-Lindau Tumor Suppressor Protein to Elongin B anc C," Science, vol. 269, No. 5229, pp. 1444-1446, Sep. 8, 1995.
Alex N. Bullock, et al, "Crystal structure of the SOCS2-elongin C-elongin B complex defines a prototypical SOCS box ubiquitin ligase," Proceedings of the National Academy of Sciences of the United States of America, vol. 103, No. 20, pp. 7637-7642, May 16, 2006.
PNAS, 1998, vol. 95, pp. 114-119. Hilton, et al.
PNAS, 1999, vol. 96, pp. 9033-9038. Botuyan, et al.
Genes & Development, 1998, vol. 12, pp. 3872-3881. Kamura, et al.
Genes & Development, 2004, vol. 18, pp. 2867-2872. Yu, et al.
Genes & Development, 2004, vol. 18, pp. 3055-3065. Kamura, et al.
Cancer Research, 2000, vol. 61, pp. 2820-2824. Kanno, et al.
Cancer Research, 2002, vol. 62, pp. 7004-7011. Murata, et al.
The EMBO J., 1996, vol. 15, pp. 5557-5566. Aso, et al.
J. Mol. Biol., 2001, vol. 312, pp. 177-186. Botuyan, et al.
Neuroscience Letters, Jul. 2005, vol. 383, pp. 28-32. Tanaka, et al.
Neuroimmunological Research, 2000, vol. 13, pp. 85-90. Kanno, et al.
Japanese Office Action dated Oct. 7, 2010 corresponding to U.S. Appl. No. 12/088,974 filed on Apr. 2, 2008.
Yamada, et al.; Transfer of the con Hippel-Lindau Gene to Neuronal Progenitor Cells in Treatment for Parkinson's Disease; Annals of Neurology, vol. No. 3, Sep. 2003, pp. 352-359.

* cited by examiner

*Primary Examiner*—Olga N Chernyshev
(74) *Attorney, Agent, or Firm*—Turocy & Watson, LLP

(57) ABSTRACT

Disclosed is a neuronal differentiation inhibitor which comprises at least one peptide capable of inhibiting or controlling the neuronal differentiation of at least one cell capable of being differentiated into a neuronal cell. The peptide is an artificially synthesized peptide which comprises a BC-box derived amino acid sequence comprising at least 10 contiguous amino acid residues selected from an amino acid sequence constituting the BC-box of at least one protein belonging to the elongin A family or comprises an amino acid sequence having a partial modification in the BC-box derived amino acid sequence.

2 Claims, No Drawings

SEQUENCE LISTING

<160> NUMBER OF SEQ ID NOS: 10

<210> SEQ ID NO 1
<211> LENGTH: 15
<212> TYPE: PRT
<213> ORGANISM: Artificial sequence
<220> FEATURE:
<223> OTHER INFORMATION: Synthetic peptide

```
<400> SEQUENCE: 1

Thr Leu His Gln Gln Cys Ile Arg Val Leu Lys Asn Asn Ile Asp
1               5                   10                  15

<210> SEQ ID NO 2
<211> LENGTH: 15
<212> TYPE: PRT
<213> ORGANISM: Artificial sequence
<220> FEATURE:
<223> OTHER INFORMATION: Synthetic peptide

<400> SEQUENCE: 2

Thr Leu Val Ser Leu Cys Gln Thr Val Leu Met Ser His Ile Asp
1               5                   10                  15

<210> SEQ ID NO 3
<211> LENGTH: 15
<212> TYPE: PRT
<213> ORGANISM: Artificial sequence
<220> FEATURE:
<223> OTHER INFORMATION: Synthetic peptide

<400> SEQUENCE: 3

Ser Leu Gln Thr Leu Cys Glu Ile Ser Leu Met Arg Asn His Ser
1               5                   10                  15

<210> SEQ ID NO 4
<211> LENGTH: 26
<212> TYPE: PRT
<213> ORGANISM: Artificial sequence
<220> FEATURE:
<223> OTHER INFORMATION: Synthetic peptide

<400> SEQUENCE: 4

Tyr Ala Arg Ala Ala Ala Arg Gln Ala Arg Ala Thr Leu His Gln Gln
1               5                   10                  15

Cys Ile Arg Val Leu Lys Asn Asn Ile Asp
            20                  25

<210> SEQ ID NO 5
<211> LENGTH: 26
<212> TYPE: PRT
<213> ORGANISM: Artificial sequence
<220> FEATURE:
<223> OTHER INFORMATION: Synthetic peptide

<400> SEQUENCE: 5

Tyr Ala Arg Ala Ala Ala Arg Gln Ala Arg Ala Thr Leu Val Ser Leu
1               5                   10                  15

Cys Gln Thr Val Leu Met Ser His Ile Asp
            20                  25

<210> SEQ ID NO 6
<211> LENGTH: 26
<212> TYPE: PRT
<213> ORGANISM: Artificial sequence
<220> FEATURE:
<223> OTHER INFORMATION: Synthetic peptide

<400> SEQUENCE: 6

Tyr Ala Arg Ala Ala Ala Arg Gln Ala Arg Ala Ser Leu Gln Thr Leu
1               5                   10                  15

Cys Glu Ile Ser Leu Met Arg Asn His Ser
            20                  25
```

```
<210> SEQ ID NO 7
<211> LENGTH: 26
<212> TYPE: PRT
<213> ORGANISM: Artificial sequence
<220> FEATURE:
<223> OTHER INFORMATION: Synthetic peptide

<400> SEQUENCE: 7

Tyr Ala Arg Ala Ala Ala Arg Gln Ala Arg Ala Thr Leu Lys Glu Arg
1               5                   10                  15

Cys Leu Gln Val Val Arg Ser Leu Val Lys
            20                  25

<210> SEQ ID NO 8
<211> LENGTH: 11
<212> TYPE: PRT
<213> ORGANISM: Artificial sequence
<220> FEATURE:
<223> OTHER INFORMATION: Synthetic peptide

<400> SEQUENCE: 8

Tyr Gly Arg Lys Lys Arg Arg Gln Arg Arg Arg
1               5                   10

<210> SEQ ID NO 9
<211> LENGTH: 11
<212> TYPE: PRT
<213> ORGANISM: Artificial sequence
<220> FEATURE:
<223> OTHER INFORMATION: Synthetic peptide

<400> SEQUENCE: 9

Tyr Ala Arg Ala Ala Ala Arg Gln Ala Arg Ala
1               5                   10

<210> SEQ ID NO 10
<211> LENGTH: 18
<212> TYPE: PRT
<213> ORGANISM: Artificial sequence
<220> FEATURE:
<223> OTHER INFORMATION: Synthetic peptide

<400> SEQUENCE: 10

Lys Gly Arg Gln Val Lys Val Trp Phe Gln Asn Arg Met Lys Trp
1               5                   10                  15

Lys Lys
```

NEURONAL DIFFERENTIATION INHIBITOR PEPTIDE AND USE THEREOF

TECHNICAL FIELD

The present invention relates to a peptide that inhibits or controls neuronal differentiation, and to a use thereof. In particular, it relates to a neuronal differentiation inhibitor having this peptide as an active ingredient.

The application claims priority from Japanese Patent Application No. 2005-293071 filed on Oct. 5, 2005, the entire content of which is incorporated herein by reference.

BACKGROUND ART

Regeneration of nerve cells is an issue in the field of regenerative medicine. For example, it is anticipated that various central nervous system disorders will be treated by nerve cell regeneration using neural stem cells or embryonic stem cells (ES cells) (see for example Japanese Patent Applications Laid-open Nos. 2004-357543 and H9-323928). However, neural stem cells are difficult to obtain (collect). Moreover, when these stem cells are transplanted as is into an affected part, they are unlikely to survive and very few differentiate into neurons. Most of those that do survive differentiate into glial cells. On the other hand, dermal stem cells, fat stem cells and other somatic (adult) stem cells are relatively easy to obtain, and if nerve cells could be differentiated from such stem cells, they would be extremely useful in the medical industry, so there is demand for development of neuronal differentiation inducers for this purpose.

However, there has been no research at all into neuronal differentiation inhibitors (or neuronal differentiation induction controllers or neuronal differentiation induction inhibitors) for artificially controlling the differentiation of stem cells and the like into neurons, making this unexplored territory. Research into neuronal differentiation (induction) inhibitors seems to be an extention of neuronal differentiation induction research.

DISCLOSURE OF THE INVENTION

It is an object of the present invention to provide a peptide capable of inhibiting neuronal differentiation (differentiation induction). Another object is to provide a neuronal differentiation inhibitor having such a peptide as an active ingredient. Another object is to design such a peptide. Another object is to provide a method for using this peptide to inhibit neuronal differentiation of target cells or to control differentiation induction thereof.

The neuronal differentiation inhibitor peptide (also called a neuronal differentiation induction inhibitor peptide) provided by the present invention is an artificially designed peptide and does not exist by itself in nature as a neuronal differentiation inhibitor peptide.

The inventors focused on Elongin A, which is known to form a complex with Elongin BC and act as a transcription control factor. For example, the following non-patent documents should be consulted:

(1) PNAS, Vol. 95, 1998, pp. 114-119
(2) Genes & Development, Vol. 12, 1998, pp. 3872-3881
(3) Genes & Development, Vol. 18, 2004, pp. 2867-2872
(4) Genes & Development, Vol. 18, 2004, pp. 3055-3065

(the entire content of these documents is incorporated by reference in this description).

The inventors completed the present invention after discovering as a result of exhaustive research that a peptide consisting of an amino acid sequence constituting all or part of a specific region called the "BC-box", which is part of the peptide chain (amino acid sequence) making up Elongin A and which is thought to bind to the Elongin BC complex, can inhibit neuronal differentiation of somatic stem cells.

The neuronal differentiation inhibitor peptide disclosed here is a peptide capable of inhibiting or controlling neuronal differentiation (induction) of at least one kind of cell that is capable of being differentiated into a neuronal cell.

That is, the present invention provides, as such a peptide, an artificially synthesized peptide which comprises a BC-box derived amino acid sequence consisting of at least 10 contiguous amino acid residues selected from an amino acid sequence constituting the BC-box of at least one protein belonging to the Elongin A family, or which comprises an amino acid sequence having a partial modification in the BC-box derived amino acid sequence.

In a preferred embodiment of the peptide disclosed here, the peptide comprises an amino acid sequence constituting a cell translocation domain at the N-terminal or C-terminal of the aforementioned BC-box derived sequence or modified sequence thereof. Desirable examples of amino acid sequences constituting cell translocation domains include those represented by SEQ ID NOS: 8, 9 and 10.

In another preferred embodiment of the peptide disclosed here, the peptide is made up of a total of 50 or fewer amino acid residues.

Another preferred embodiment of the peptide disclosed here comprises, as the BC-box derived sequence, any of the amino acid sequences represented by SEQ ID NOS: 1 to 3, or such an amino acid sequence having a partial modification in the aforesaid sequence.

The present invention also provides an artificially designed polynucleotide not present in nature which comprises a nucleotide sequence coding for any of the neuronal differentiation inhibitor peptides disclosed here and/or a nucleotide sequence complementary to such a sequence (for example, a polynucleotide effectively consisting of such a sequence).

An example of a desirable polynucleotide is a polynucleotide containing a nucleotide sequence (for example, a polynucleotide effectively consisting of such a sequence) that for any of the amino acid sequences represented by SEQ ID NOS: 1 to 6 (or an amino acid sequence obtained by partial modification of such a sequence), or a nucleotide sequence complementary to such a sequence.

The present invention also provides a neuronal differentiation inhibitor (also called a neuronal differentiation induction inhibitor) containing at least one neuronal differentiation inhibitor peptide disclosed here.

That is, the neuronal differentiation inhibitor disclosed here contains an artificially synthesized peptide which comprises a BC-box derived amino acid sequence consisting of at least 10 contiguous amino acid residues selected from an amino acid sequence constituting the BC-box of at least one protein belonging to the Elongin A family, or which comprises an amino acid sequence having a partial modification in the BC-box derived amino acid sequence.

Preferably, this peptide comprises a cell translocation domain at the N-terminal or C-terminal of the aforementioned BC-box derived sequence or modified sequence thereof.

A neuronal differentiation inhibitor is preferred that has as an active ingredient the aforementioned peptide wherein the total number of amino acid residues is 50 or fewer.

A neuronal differentiation inhibitor is also preferred that has as an active ingredient a peptide that comprises, as the BC-box derived sequence, any of the amino acid sequences represented by SEQ ID NOS: 1 to 3, or such an amino acid sequence having a partial modification in the aforesaid sequence.

The neuronal differentiation inhibitor disclosed here typically comprises 1 or 2 or more neuronal differentiation inhibitor peptides together with a pharmacologically acceptable carrier.

Another aspect of the invention provides a method for producing the neuronal differentiation inhibitor peptide disclosed here. This method includes designing a peptide chain which comprises a BC-box derived amino acid sequence consisting of at least 10 contiguous amino acid residues selected from an amino acid sequence constituting the BC-box of at least one protein belonging to the Elongin A family, or which comprises such an amino acid sequence having a partial modification in the BC-box derived amino acid sequence, and which is capable of inhibiting or controlling the neuronal differentiation of at least one kind of cell capable of being differentiated into a neuronal cell, and also includes synthesizing the designed peptide chain.

Preferably a peptide chain is designed to contain an amino acid sequence constituting a cell translocation domain at the N-terminal or C-terminal of the aforementioned BC-box derived amino acid sequence or modified amino acid sequence thereof.

Moreover, the peptide chain is preferably designed so that the total number of amino acid residues making up the peptide chain is 50 or fewer.

Another aspect of the present invention provides various methods for using the neuronal differentiation inhibitor peptide disclosed here.

As one such method, the present invention provides a method for inhibiting neuronal differentiation (differentiation induction) of target cells in a living body or living tissue.

That is, this method includes preparing an artificially synthesized peptide which comprises a BC-box derived amino acid sequence consisting of at least 10 contiguous amino acid residues selected from an amino acid sequence constituting the BC-box of at least one protein belonging to the Elongin A family, or which comprises an amino acid sequence having a partial modification in the BC-box derived amino acid sequence, and supplying this peptide to a living body or to living tissue that has been temporarily or permanently removed from the body.

In a preferred embodiment of this method, the peptide comprises an amino acid sequence constituting a cell translocation domain at the N-terminal or C-terminal of the aforementioned BC-box derived sequence or modified sequence thereof.

In another preferred embodiment, the peptide is made up of a total of 50 or fewer amino acid residues.

In yet another preferred embodiment, the peptide comprises, as the BC-box derived sequence, any of the amino acid sequences represented by SEQ ID NOS: 1 to 3, or such an amino acid sequence having a partial modification in the aforesaid sequence.

The peptide which is the active ingredient in the neuronal differentiation inhibitor of the present invention can be easily produced because it is a synthetic peptide comprising the aforementioned BC-box derived amino acid sequence or an amino acid sequence having a partial modification in the BC-box derived amino acid sequence. Consequently, it is easy to prepare the desired quantity of peptide (and therefore of neuronal differentiation inhibitor).

(Sequence Table Free Text)

SEQ ID NOS: 1 to 10 Synthetic peptides

BEST MODE FOR CARRYING OUT IN INVENTION

Preferred embodiments of the present invention are explained below. Apart from matters that are specifically mentioned in this description (such as the primary structure and chain length of the neuronal differentiation inhibitor peptide), other matters which are necessary for implementing the present invention (for example, general matters related to peptide synthesis, polynucleotide synthesis and preparation of a neuronal differentiation inhibitor (drug composition) having the peptide as a component) can be understood by those skilled in the art as design matters based on prior art in the fields of medicine, pharmacology, organic chemistry, biochemistry, genetic engineering, protein engineering, molecular biology, hygiene and the like. The present invention can be implemented based on what is disclosed in this description and on technical common knowledge in these fields. In the following explanation, amino acids are described with single-letter codes in accordance with the rules of nomenclature for amino acids set forth in the IUPAC-IUB guidelines, but in the sequence listings they are given three-letter codes.

The entire content of all documents cited in this description is incorporated by reference in this description.

In this description, an "artificially synthesized neuronal differentiation inhibitor peptide" means a peptide chain that does not exist stably and independently in the natural world and so that has been produced by artificial chemical or biological synthesis (that is, based on genetic engineering), and that can exist stably in a specific system (for example, in the composition of a neuronal differentiation inhibitor).

In this description, the term "peptide" indicates an amino acid polymer having multiple peptide bonds, and is not limited by the number of amino acid residues contained in the peptide chain. Consequently, oligopeptides containing as few as 10 amino acid residues and polypeptides consisting of more amino acid residues are all considered neuronal differentiation inhibitor peptides in this description.

Unless otherwise specified, the term "amino acid residue" in this description encompasses the N-terminal amino acid and C-terminal amino acid of the peptide chain.

In this description, an "amino acid sequence having a partial modification (modified amino acid sequence)" for a specified amino acid sequence is an amino acid sequence formed by substituting, deleting and/or adding (inserting) 1 or several (such as 9 or fewer, preferably 5 or fewer, or more preferably 2 or 3) amino acid residues without sacrificing the neuronal differentiation (induction) inhibiting ability of the specified amino acid sequence. Typical examples include a sequence obtained by conservative amino acid replacement in which 1 or several (typically 2 or 3) amino acids are conservatively replaced (such as a sequence in which basic amino acids are replaced with other basic amino acids), or a sequence consisting of the specified amino acid sequence with 1 or several (typically 2 or 3) amino acid residues added (inserted) or deleted.

In this description, the term "polynucleotide" indicates a polymer (nucleic acid) comprising multiple nucleotides bound by phosphodiester bonds, with no limit on the number of nucleotides. DNA fragments and RNA fragments of various lengths are considered polynucleotides in this description. An "artificially designed polynucleotide" means that the (full-length) nucleotide chain is one that cannot exist independently in nature, and the polynucleotide has been artificially synthesized by chemical synthesis or biosynthesis (that is, produced based on genetic engineering techniques).

The inventors in this case have identified an amino acid sequence which is present in the BC-box, a region (domain or motif) binding to the Elongin BC complex (specifically, to part of the amino acid sequence of Elongin C), and which is capable of inhibiting neuronal differentiation (induction) even as a relatively short, artificially synthesizable peptide chain, along with a peptide consisting of this sequence.

Typical examples are SEQ ID NOS: 1 to 3, which are amino acid sequences contained in the BC-boxes of proteins that have been identified as Elongin A in different species (see Non-Patent Document 2).

Specifically, these are amino acid sequences consisting of 15 contiguous amino acid residues from the N-termini of BC-boxes contained in human derived EloA (SEQ ID NO: 1), C. elegans derived EloA (SEQ ID NO: 2) and S. cerevisiae derived EloA (SEQ ID NO: 3) (see non-patent document 2), as well as peptides consisting of these sequences.

These are only examples, and are not intended to limit the constituent amino acid sequence of the Elongin A BC-box of the present invention.

In the present invention, as a neuronal differentiation inhibitor peptide can be preferably used a peptide consisting of at least 10 contiguous amino acid residues (such as the 10 amino acid residues at the N-terminal end of an amino acid sequence) selected from amino acid sequences that are assigned with SEQ ID NOS and shown in the sequence listings attached to this description.

Can also be used as a neuronal differentiation inhibitor peptide a suitable modified sequence based on an amino acid sequence consisting of at least 10 contiguous amino acid residues (preferably an amino acid sequence consisting of 10 to 15 contiguous amino acid residues) selected from an amino acid sequence given in the sequence listings can also be used as a neuronal differentiation inhibitor peptide.

For example, of the amino acid sequences consisting of 14 or 15 contiguous amino acid residues from the N-terminals of the BC-boxes represented by the SEQ ID NOS, a desirable is an amino acid sequence with multiple amino acid residues deleted therefrom, such as an amino acid sequence consisting of 10, 11, 12 or 13 contiguous amino acid residues from the N-terminal of the BC-box represented by each SEQ ID NO (or in other words modified amino acid sequence obtained by deleting multiple amino acid residues at the C-terminal end of the BC-box represented by each SEQ ID NO), constituting a peptide with neuronal differentiation (induction) inhibiting ability.

Alternatively, a preferred amino acid sequence can be obtained by adding multiple amino acid residues to the C-terminal end of the amino acid sequence consisting of 14 or 15 contiguous amino acid residues from the N-terminal of the BC-box represented by teach SEQ ID NO.

A neuronal differentiation inhibitor peptide may consist only of the aforementioned BC-box derived amino acid sequence or modified amino acid sequence thereof (hereunder called generally a "BC-box related sequence"), but preferably has introduced therein an amino acid sequence constituting a so-called cell translocation domain (protein transduction domain) so as to improve neuronal differentiation (induction) inhibiting ability. When a peptide having such a domain (motif) is supplied to a specific cell material (target cells), it can penetrate rapidly inside the cells, thereby enhancing the neuronal differentiation inhibitor activity.

Many suitable cell translocation domains (peptide fragments) are known, but certain suitable examples are represented by SEQ ID NOS: 8, 9 and 10. SEQ ID NO: 8 represents the amino acid sequence of a protein transduction domain contained in the TAT of HIV, and a peptide consisting of that sequence. SEQ ID NO: 9 represents the amino acid sequence of a protein transduction domain (PTD4) obtained by modification of this TAT, and a peptide consisting of this sequence. SEQ ID NO: 10 represents an amino acid sequence associated with the ANT of Drosophila mutant Antennapedia, and a peptide consisting of this sequence.

The neuronal differentiation inhibitor peptide provided by the invention preferably has at least one amidated amino acid residue. Amidation of a carboxyl group of an amino acid residue (typically the C-terminal amino acid residue of the peptide chain) serves to improve the structural stability (such as protease resistance) of the neuronal differentiation inhibitor peptide.

In the neuronal differentiation inhibitor peptide, the peptide chain preferably consists of a total of 100 or fewer (or more preferably 50 or fewer or still more preferably 30 or fewer) amino acid residues. Such a short peptide is easy to chemically synthesize, so that the neuronal differentiation inhibitor peptide can be easily provided. The peptide conformation (spatial structure) is not particularly limited as long as the neuronal differentiation (induction) inhibiting ability is retained under given conditions of use, but a straight chain or helix is preferred because it is less likely to be immunogenic (antigenic). Peptides having such a shape hardly constitute epitopes. For these reasons, a neuronal differentiation inhibitor peptide for application to a neuronal differentiation inhibitor is preferably a straight-chain peptide with a relatively low molecular weight (consisting of typically 50 or fewer or especially 30 or fewer amino acids).

The percentage of the total amino acid sequence that consists of the BC-box related sequence (that is, the number of amino acid residues making up the BC-box related sequence part as a percentage of the total number of amino acid residues in the peptide chain) is not particularly limited as long as neuronal differentiation (induction) inhibitor activity is retained, but is preferably 50% or more. It is desirable that all the amino acid residues in the neuronal differentiation inhibitor peptide be L-type amino acids, but some or all of the amino acid residues may also be replaced with D-type amino acids to the extent that the neuronal differentiation (induction) inhibitor activity is not adversely affected.

The neuronal differentiation inhibitor peptide of the present invention may include partial sequences that do not form part of the neuronal differentiation inhibitor related sequence to the extent that these do not detract from neuronal differentiation (induction) inhibitor ability. These are not particularly limited, but a desirable example is a sequence capable of maintaining the 3-dimensional shape (typically the straight-chain shape) of the BC-box related sequence part.

Of the neuronal differentiation inhibitor peptides disclosed here, those with relatively short peptide chains can be easily synthesized by ordinary methods of chemical synthesis. For example, conventional solid phase synthesis methods or liquid phase synthesis methods may be adopted. Solid phase synthesis using Boc (t-butyloxycarbonyl) or Fmoc (9-fluorenylmethoxycarbonyl) as the amino protecting group is suitable.

For the neuronal differentiation inhibitor peptide, a peptide chain having the desired amino acid sequence and a modified (C-terminal amidated, etc.) part can be synthesized by solid phase synthesis using a commercial peptide synthesizer (available for example from PerSeptive Biosystems, Applied Biosystems or the like).

Alternatively, the neuronal differentiation inhibitor peptide can be biosynthesized by genetic engineering methods. This approach is suitable when producing polypeptides with relatively long peptide chains. That is, DNA is synthesized with a nucleotide sequence (including ATG initiation codon) coding for the amino acid sequence of the desired neuronal differentiation inhibitor peptide. A recombinant vector having a gene expression construct consisting of this DNA together with the various regulatory elements (including promoters, ribosome binding sites, terminators, enhancers, and various cis-elements for controlling expression level) required for expressing the amino acid sequence in host cells is then constructed according to the host cells.

A common technique is to introduce this recombinant vector into specific host cells (such as yeast cells, insect cells, plant cells or animal (mammal) cells), and then culture these host cells, or a tissue or organism containing these cells, under specific conditions. In this way, the target polypeptide can be expressed and produced in the cells. The polypeptide is then isolated and purified from the host cells (or from medium if it is excreted) to thereby obtain the target neuronal differentiation inhibitor peptide.

Methods conventionally used in the field can be adopted for constructing the recombinant vector and introducing the constructed vector into host cells, and these methods themselves are not explained in detail because they do not characterize the invention.

For example, a fused protein expression system can be used in order to achieve efficient, high-volume production in host cells. That is, a gene (DNA) coding for the amino acid sequence of the target neuronal differentiation inhibitor peptide is chemically synthesized, and this synthetic DNA is introduced into a suitable site in a suitable fused protein expression vector (for example, a GST (Glutathione S-transferase) fused protein expression vector such as a Novagen pET series or Amersham Biosciences pGEX series vector). Host cells (typically E. coli) are then transformed with this vector. The resulting transformant is cultured to prepare the target fused protein. The protein is extracted and purified. The resulting purified fused protein is cleaved with a specific enzyme (protease), and the released target peptide fragment (designed neuronal differentiation inhibitor peptide) is collected by a method such as affinity chromatography. The neuronal differentiation inhibitor peptide of the present invention can be produced using such a conventional fused protein expression system (using for example a GST/H is system from Amersham Biosciences).

Alternatively, template DNA (that is, a synthetic DNA fragment comprising a nucleotide sequence coding for the amino acid sequence of the neuronal differentiation inhibitor peptide) for a cell-free protein synthesis system can be constructed, and the target polypeptide can be synthesized in vitro by means of a cell-free protein synthesis system using various compounds (ATP, RNA polymerase, amino acids, etc.) necessary for peptide synthesis. The papers of Shimizu et al. (Shimizu et al., Nature Biotechnology, 19, 751-755 (2001)) and Madin et al. (Madin et al., Proc. Natl. Acad. Sci. USA, 97(2), 559-564 (2000)) can be consulted with respect to cell-free protein synthesis systems. As of the time of this application many companies were involved in contract production of polypeptides based on the techniques described in these papers, and cell-free protein synthesis kits (for example, the Proteios® Wheat germ cell-free protein synthesis kit, available from Toyobo, Japan) are commercially available.

Consequently, as discussed above, once the amino acid sequence to be used (BC-box related sequence) has been determined, and a peptide chain designed, the target neuronal differentiation inhibitor peptide can be easily synthesized and produced with a cell-free protein synthesis system based on the amino acid sequence. For example, the neuronal differentiation inhibitor peptide of the present invention can be easily produced based on a Puresystem® from the Post Genome Institute in Japan.

A single-stranded or double-stranded polynucleotide comprising a nucleotide sequence coding for the neuronal differentiation inhibitor peptide disclosed here and/or a nucleotide sequence complementary to that sequence can be easily produced (synthesized) by conventional methods. That is, by selecting codons corresponding to each of the amino acid residues making up the designed amino acid sequence, a nucleotide sequence corresponding to the amino acid sequence of the neuronal differentiation inhibitor peptide can be easily determined and provided. Once the nucleotide sequence has been determined, a polynucleotide (single strand) corresponding to the desired nucleotide sequence can be easily obtained using a DNA synthesizer or the like. The resulting single-stranded DNA can then be used as a template to obtain the target double-stranded DNA by various enzyme synthesis means (typically PCR).

A polynucleotide provided by the present invention may be in the form of either DNA or RNA (mRNA or the like). It can be provided as a double strand or single strand. If provided as a single strand, it may be either a coding strand (sense strand) or the non-coding strand (antisense strand) of the complementary sequence.

As discussed above, a polynucleotide provided by the present invention can be used as a material for constructing a recombinant gene (expression cassette) for producing the neuronal differentiation inhibitor peptide in various host cells or in a cell-free protein synthesis system.

The present invention provides a polynucleotide comprising a nucleotide sequence coding for a neuronal differentiation inhibitor peptide having a novel amino acid sequence, and/or a nucleotide sequence complementary to that sequence. For example, it provides an artificially designed polynucleotide comprising (or effectively consisting of) a nucleotide sequence coding for an amino acid sequence represented by any of SEQ ID NOS: 1 to 6 wherein the total number of amino acid residues in the peptide chain is 50 or fewer (preferably 30 or fewer), or a modified sequence thereof (neuronal differentiation inhibitor related sequence), and/or a nucleotide sequence complementary to that sequence.

A preferred neuronal differentiation inhibitor peptide of the present invention can inhibit or control the neuronal differentiation of at least one kind of cell capable of differentiation into a neuronal cell. Consequently, it can be used favorably as the active ingredient of a neuronal differentiation inhibitor. The neuronal differentiation inhibitor peptide contained in a neuronal differentiation inhibitor may also be in the form of a salt to the extent that this does not detract from the neuronal differentiation inhibitor activity. For example, it is possible to use an acid addition salt of the peptide, which can be obtained by addition reaction of an inorganic acid or organic acid commonly used in ordinary methods. Another salt (such as a metal salt) is also possible as long as it has neuronal differentiation inhibitor activity.

The neuronal differentiation inhibitor can also contain various medicinally (pharmacologically) acceptable carriers according to the form of use in addition to the neuronal differentiation inhibitor peptide that is the active ingredient. Carriers that are commonly used in peptide drugs are preferred for the diluents, excipients and the like. These may differ depending on the use and form of the neuronal differentiation inhibitor, but typical examples include water, physiological buffers and various organic solvents. Aqueous alcohol (such as ethanol) solutions of a suitable concentration, glycerol, olive oil and other non-drying oils are also possible, as are liposomes. Secondary ingredients that may be included in the neuronal differentiation inhibitor include various fillers, extenders, binders, humectants, surfactants, colorants, fragrances and the like.

The form of the neuronal differentiation inhibitor is not particularly limited. Typical forms include liquids, suspensions, emulsions, aerosols, foams, granules, powders, pills, capsules, ointments and the like. It may also be a freeze-dried product or granules to be dissolved immediately before use in saline or a suitable buffer (such as PBS) for use in an injection.

The processes used to prepare drugs (compositions) of various forms using the neuronal differentiation inhibitor peptide (main ingredient) and various carriers (secondary ingredients) as the materials may be those used in well-known conventional methods, and the preparation methods themselves are not explained in detail here because they do not characterize the invention. One source of information on prescriptions is Comprehensive Medicinal Chemistry, Corwin Hansch Ed., Pergamon Press Pub. (1990) for example.

The neuronal differentiation inhibitor provided by the invention can be used in various ways and at various doses depending on the form and object.

For example, the neuronal differentiation inhibitor peptide containing a BC-box related sequence disclosed here (that is, a neuronal differentiation inhibitor containing this peptide) can be administered in the desired dosage to a patient (living body) as a liquid by intravenous, intramuscular, subcutaneous, intracutaneous or intraperitoneal injection. It may also be administered orally in pill or other solid form. In this way, it is possible to inhibit or control the differentiation into neurons of target cells such as somatic stem cells that are typically located in or around a diseased part in the living body.

Thus, induction of differentiation of target cells into neurons can be artificially controlled through combined use with a neuronal differentiation inducer for example. Consequently, various neural diseases for which neural regeneration is a useful therapy can be effectively treated. For example, treatment by a regenerative medicine approach is possible for Parkinson's disease, stroke, Alzheimer's disease, physical paralysis due to spinal cord damage, brain contusion, amyotrophic lateral sclerosis, Huntington's disease, brain tumors and other neural diseases.

It is clear from the explanation above that by using any of the neuronal differentiation inhibitor peptides disclosed here, the present invention can provide cells, cell clusters or live tissue in which induction of differentiation into neurons is controlled at a specific level, making them useful for treating neural disease.

A polynucleotide coding for the neuronal differentiation inhibitor peptide of the present invention can be used as a material for so-called gene therapy. For example, a gene (typically a DNA fragment or RNA fragment) coding for the neuronal differentiation inhibitor peptide can be incorporated into a suitable vector, and introduced into the target site to thereby cause constant expression of the neuronal differentiation inhibitor peptide of the present invention in a living body (cells). Consequently, a polynucleotide (DNA fragment, RNA fragment) coding for the neuronal differentiation inhibitor peptide of the present invention is useful as a drug for treatment or prevention of neural disease.

Several examples of the present invention are described below, but the present invention is not intended to be limited to these examples.

Example 1

Peptide Synthesis

A total of 4 peptides (samples 1 to 3, comparative sample 1) were produced using the peptide synthesizer described below. Table 1 lists the amino acid sequences of these synthetic peptides.

TABLE 1

| Sample No. | Amino acid sequence | SEQ ID NO | Total number of amino acid residues |
|---|---|---|---|
| Sample 1 | YARAAARQARA-TLHQQCIRVLKNNID | 4 | 26 |
| Sample 2 | YARAAARQARA-TLVSLCQTVLMSHID | 5 | 26 |
| Sample 3 | YARAAARQARA-SLQTLCEISLMRNHS | 6 | 26 |
| Comparative sample 1 | YARAAARQARA-TLKERCLQVVRSLVK | 7 | 26 |

As shown in Table 1, samples 1 to 3 and comparative sample 1 all consist of a total of 26 amino acid residues and contain a membrane translocation domain PTD4 (SEQ ID NO: 9) on the N-terminal side. Adjacently, to the C-terminal side, samples 1 to 3 contain a BC-box related sequence. In particular, samples 1 (peptide of SEQ ID NO: 4), 2 (peptide of SEQ ID NO: 5), and 3 (peptide of SEQ ID NO: 6) comprise an amino acid sequence composed of 15 contiguous amino acid residues from the N-terminal of the BC-box present in, respectively, human elongin-A (SEQ ID NO: 1), C. elegance elongin-A (SEQ ID NO: 2), and S. cerevisiae elongin-A (SEQ ID NO: 3). On the other hand, comparative sample 1 (peptide of SEQ ID NO: 7) has, to the C-terminal side, an amino acid sequence composed of 15 contiguous amino acid residues, the 157th residue through the 171st residue of the amino acid sequence of a VHL (von Hippel-Lindau) protein that shows neuronal differentiation-inducing activity.

The C-terminal carboxyl group (—COOH) is amidated (—CONH$_2$) in all of these samples.

Each of these peptides was prepared by solid phase synthesis (Fmoc chemistry) using a commercial peptide synthesizer (model 433A from Applied Biosystems). HATU (available from Applied Biosystems) was used as the coupling agent. The resin and amino acids used in the solid phase synthesis were purchased from Novabiochem. For those amidated at the C-terminal, Rink Amide resin (100-200 mesh) was used as the solid support.

Each synthetic peptide with the desired length was obtained by extending the peptide chain from Fmoc amino acid linked to the resin by repeating deprotection and condensation reactions following the protocol of the peptide synthesizer. In particular, the following process was repeated: cleavage and removal of Fmoc, the amino protecting group on the amino acid, with 20% piperidine/dimethylformamide (DMF) (peptide synthesis grade, from Kanto Chemical Co., Inc.); washing with DMF; reaction with 4 equivalences of Fmoc-amino acid (—OH); washing with DMF. After the chain-extension reaction on the peptide chain had been completed, the Fmoc group was cleaved off with 20% piperidine/DMF and the aforementioned reaction product was washed in sequence with DMF and methanol.

After the solid phase reaction, the resin with the synthesized peptide was transferred to a centrifuge tube; 1.8 ml ethanediol, 0.6 mL m-cresol, 3.6 mL thioanisole, and 24 mL trifluoroacetic acid were added; and stirring was carried out for 2 hours at room temperature. The resin to which the peptide chain had been bound was removed by filtration.

Cold ethanol was added to the filtrate and a peptide precipitate was obtained by cooling on ice-cooled water. The supernatant obtained by centrifugation (2500 rpm, 5 minutes) was then discarded. Cold diethyl ether was added to the precipitate. After thorough stirring was carried out; centrifugation was carried out under the previously mentioned conditions. This step of stirring and centrifuging was repeated three times in total.

The obtained peptide precipitate was dried under vacuum and was purified by high performance liquid chromatography (Waters 600 from Waters).

Specifically, a pre-column (Guard-Pak Delta-pak C18 A300 from Nihon Waters K.K.) and a C18 reverse-phase column (Nihon Waters K.K., XTerra (registered trademark) column, MS C18, 5 μm, 4.6×150 mm) were used, and a mixture of 0.1% aqueous trifluoroacetic acid solution and a solution of 0.1% trifluoroacetic acid in acetonitrile was used as the elutant. That is, separation/purification was carried out over 30 to 40 minutes on the previously cited column at a flow rate of 1.5 mL/minute while carrying out a timewise increase in the proportion of the trifluoroacetic acid/acetonitrile solution in the eluent (a concentration gradient from 10% to 80% as the volumetric ratio was set up). The peptide eluting from the reverse-phase column was detected at a wavelength of 220 nm using an ultraviolet detector (490E Detector, Waters Corporation) and recorded as a peak on the recoding chart.

The molecular weight of each eluted peptide was determined based on matrix-assisted laser desorption time-of-flight mass spectrometry (MALDI-TOF/MS) using a Voyager DE RP (trade name) from PerSeptive Biosystems. The results confirmed the synthesis and purification of the target peptide.

Example 2

Evaluation of the Neuronal Differentiation Inhibitor Activity of the Synthetic Peptides Each sample obtained in example 1 was analyzed for the neuronal differentiation inhibitor activity.

In particular, each sample peptide together with the peptide of comparative sample 1 (hereinafter referred to as VHL peptide) was added to and incubated in a culture of adipose stem cells procured from humans. The addition concentration of each peptide was about 100 ng/mL. For comparison, a culture containing VHL peptide alone was incubated in a similar manner.

At 24 hours after peptide addition, evaluation was carried out by a standard immune antibody procedure. Specifically, MAPs (microfilament associated proteins) and NeuN (neuronal nuclei) were added as neuron markers, and the degree of neuronal differentiation was evaluated by confocal laser microscopy. MAPs is a marker that can stain (detect) broadly, from relatively immature neurons to mature neurons. NeuN is a marker that can specifically stain (detect) mature neurons.

The results confirmed significant neuronal differentiation in the experiment with VHL peptide alone. On the other hand, in the experiments wherein VHL peptide and any one of samples 1, 2, and 3 were added together, no significant neuronal differentiation was observed. This indicates that neuronal differentiation-inducing activity of VHL peptide was inhibited by the addition of the peptide of the present invention.

Hence, as another aspect, the present invention provides a method for controlling (inhibiting), by addition of an appropriate amount of a neuronal differentiation inhibitor peptide of this invention, the neuronal differentiation-inducing activity of VHL peptide or other neuronal differentiation-inducer (typically, a neuronal differentiation-inducing peptide) transported to a subject (e.g., tissue of a patient or tissue cultured in vitro) from the outside; or the activity of a neuronal differentiation-inducer produced in the subject body.

Example 3

Preparation of Granules 50 mg of the sample 1 peptide, 50 mg microcrystalline cellulose, and 400 mg lactose are mixed; 1 mL of a mixed solution of ethanol and water are added; and mixing/kneading is carried out. The resulting mixture can then be granulated by a standard method to obtain granules (granular neuronal differentiation inducer) in which the neuronal differentiation-inducing peptide is the principal component.

While specific examples of the present invention have been described in detail in the preceding, these are merely examples and do not limit the scope of the claims. The various modifications and alterations of the specific examples provided as examples above are encompassed in the technology described in the claims.

INDUSTRIAL APPLICABILITY

According to the present invention, in the field of healthcare, medicine, or biology, differentiation (induction of differentiation) into neuronal cells of target cells (cells that can be induced to differentiate into neuronal cells; for example, adipose cells, somatic stem cells such as skin stem cells or embryonic stem cells) can be inhibited or controlled. Abnormal differentiation (induction of differentiation) of a nerve in a living body can also be inhibited. As described above, the neuronal differentiation inhibitor peptide of the present invention exhibits an excellent neuronal differentiation inhibitor activity and thus can be utilized as a pharmaceutical peptide component.

The invention claimed is:

1. A method for inhibiting neuronal differentiation of target cells into neuronal cells in a living body or live tissue, the method comprising
administering an artificially synthesized peptide which comprises an amino acid sequence represented by SEQ ID NO: 1 to a living body or to live tissue that has been removed from the living body.

2. The method according to claim 1, wherein the peptide is made up of a total of 50 or fewer amino acid residues.

* * * * *